United States Patent
Hegde et al.

(10) Patent No.: US 11,666,306 B2
(45) Date of Patent: Jun. 6, 2023

(54) DEVICE AND METHOD FOR DETECTING MISUSE OF A MEDICAL IMAGING SYSTEM

(71) Applicant: KONINKLIJKE PHILIPS N.V., Eindhoven (NL)

(72) Inventors: Sanjay Ramachandra Hegde, Bangalore (IN); Pallavi Vajinepalli, Bangalore (IN); Ganesan Ramachandran, Bangalore (IN); Subhendu Seth, Bangalore (IN); Ishank Jain, Bangalore (IN); Srikanth Shettigar, Bangalore (IN); Anumod Odungattu Thodiyil, Bangalore (IN); Sindhu Priyadarshini Nellur Prakash, Bangalore (IN); Celine Firtion, Surat (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 666 days.

(21) Appl. No.: 16/635,398

(22) PCT Filed: Jul. 27, 2018

(86) PCT No.: PCT/EP2018/070515
§ 371 (c)(1),
(2) Date: Jan. 30, 2020

(87) PCT Pub. No.: WO2019/025332
PCT Pub. Date: Feb. 7, 2019

(65) Prior Publication Data
US 2020/0155115 A1    May 21, 2020

(30) Foreign Application Priority Data

Jul. 31, 2017  (EP) .................................. 17183946
Aug. 2, 2017   (IN) ............................. 201744027424

(51) Int. Cl.
*A61B 8/08*      (2006.01)
*G16H 10/60*     (2018.01)
(Continued)

(52) U.S. Cl.
CPC ............ *A61B 8/0866* (2013.01); *A61B 8/085* (2013.01); *A61B 8/5223* (2013.01); *A61B 8/565* (2013.01);
(Continued)

(58) Field of Classification Search
CPC ..... A61B 8/0866; A61B 8/085; A61B 8/5223; A61B 8/565; A61B 8/00; A61B 8/08;
(Continued)

(56) References Cited

U.S. PATENT DOCUMENTS

2008/0270177 A1   10/2008   Chamberlain
2009/0216564 A1    8/2009   Rosenfeld
(Continued)

FOREIGN PATENT DOCUMENTS

CN   1915177   *  2/2007  ............... A61B 8/00
CN   1915177 A    2/2007
(Continued)

OTHER PUBLICATIONS

International Search and Written Opinion for International Application No. PCT/EP2018/070515, filed Jul. 27, 2018, 14 pages.
(Continued)

*Primary Examiner* — Amara Abdi (57) ABSTRACT

The present invention relates to a device (10) for detecting a misuse of a medical imaging system (20), comprising a data interface (12) for acquiring medical image data (24) and audit log data (26) from the medical imaging system (20); a processing unit (14) which is configured to configured to analyse the medical image data (24) to determine whether or not a part of a fetus is imaged in the medical image data (24),
(Continued)

to compare the medical image data (24) and the audit log data (26) with each other, and to determine based on said comparison whether there is a mismatch between the medical image data (24) and the audit log data (26); and a feedback unit (16) which is configured to generate a misuse alert signal if a mismatch is detected by the processing unit (14).

15 Claims, 5 Drawing Sheets

(51) Int. Cl.
  *G16H 30/40* (2018.01)
  *G16H 40/63* (2018.01)
  *A61B 8/00* (2006.01)
(52) U.S. Cl.
  CPC ............ *G16H 10/60* (2018.01); *G16H 30/40* (2018.01); *G16H 40/63* (2018.01)
(58) Field of Classification Search
  CPC .......... A61B 8/46; G16H 10/60; G16H 30/40; G16H 40/63; G16H 10/00; G16H 50/30
  See application file for complete search history.

(56) References Cited

U.S. PATENT DOCUMENTS

| | | |
|---|---|---|
| 2012/0269412 A1 | 10/2012 | Guan et al. |
| 2015/0173715 A1* | 6/2015 | Raghavan .............. G16H 40/67 600/443 |
| 2015/0342560 A1 | 12/2015 | Davey et al. |
| 2016/0092748 A1* | 3/2016 | Koktava ................ G06V 10/75 382/128 |
| 2016/0317127 A1 | 11/2016 | dos Santos Mendonca et al. |

FOREIGN PATENT DOCUMENTS

| | | |
|---|---|---|
| CN | 102783972 A | 11/2012 |
| WO | 2014117096 A1 | 7/2014 |
| WO | 2015105619 A9 | 7/2015 |

OTHER PUBLICATIONS

European Search Report for European Patent Application No. EP17183946, filed Jul. 31, 2017, 2 pages.
Dr. Smitha Mishra, "Fetal Sex Disclosure : Do we need alternative view on PCPNDT Act", Medical Dialogues, Published Feb. 24, 2016, 1 page (Abstract).

* cited by examiner

DEVICE AND METHOD FOR DETECTING MISUSE OF A MEDICAL IMAGING SYSTEM

RELATED APPLICATIONS

This application is the U.S. National Phase application under 35 U.S.C. § 371 of International Application No. PCT/EP2018/070515, filed on Jul. 27, 2018, which claims priority to and the benefit of both European Application No. 17183946.7, filed Jul. 31, 2017, and Indian Application No. 201744027424 filed Aug. 2, 2017. These applications are hereby incorporated by reference herein.

FIELD OF THE INVENTION

The present invention relates to a device for detecting a misuse of a medical imaging system. The present invention also relates to a corresponding method and computer program. The herein described device, method and computer program are particularly intended for preventing misuse of medical imaging systems for gender detection in countries where this is prohibited.

BACKGROUND OF THE INVENTION

Current medical imaging systems, such as e.g. ultrasound imaging systems, allow clinicians to conduct scans on patients, capture images, make measurements, and use built-in algorithms. Ultrasound imaging is becoming a mainstay of prenatal and obstetric practice as it is an established technique for non-invasive examination of fetuses.

However, many countries have laws in place to restrict the use of ultrasound by an expert for the purpose of medical diagnosis only. In some countries only licensed personnel may perform a fetal scan. India is an example for such a country.

Over the past four decades, the increasing availability of ultrasound equipment has assisted India's cultural preference for sons and distorted the sex ratio across the nation. According to the census in 2011, male to female ratio in some of the Indian states is as high as 113%. Hence, in India, prenatal sex determination is prohibited by law under the so-called Pre-Conception and Pre-Natal Diagnostic Techniques (PC-PNDT) act. All ultrasound systems in India are now under the ambit of PC-PNDT act. Under this act, a facility having ultrasound imaging equipment is required to maintain elaborate records of the prenatal screening carried out with the equipment and, thereby, be able to provide proof to the relevant authorities that it was not used for fetal sex determination.

Even when the facilities are performing non-obstetric scans, like ultrasound scans for cardiology, oncology, etc., they still need to maintain elaborate records increasing complexity and cost of ownership. With the availability of ultra mobile ultrasound systems and the advances in ultrasound technology, there is an immense scope to increase the use of ultrasound to non-traditional users beyond obstetric purposes, like point of care, emergency, critical care, etc. However, laws such as PC-PNDT are limiting adoption of new technology for these new use cases.

Currently, ultrasound imaging in India is conducted by clinicians including but not limited to radiologists, sonographers, obstetricians, gynecologists, cardiologists, ophthalmologists, etc. Such clinicians are allowed to conduct a fetal scan and per law it is illegal for them to disclose the gender of the fetus.

Nevertheless, there is no sufficient security measure in place to check who used the ultrasound system and what procedure was conducted. Moreover, trained personnel can conduct a sex determination test in rather short time. This in turn means that the Indian Government as well as the government of other countries having similar laws do not have sufficient measures and data to enforce the law.

Video- and GPS-based solutions are available in the market capable of recording the procedure and/or the location of the scan being conducted. These solutions are capable of streaming and storing the images for audit purposes. However, they are subject to tampering and require manual intervention which makes them non-scalable.

CN 102783972 A discloses a system for monitoring identification of the gender of a fetus without medical needs. A monitor is used for monitoring the work state of the ultrasonic apparatus, and the ultrasound images are analysed. The system provides image evidence of identification of the gender of the fetus, such that official authorities have a proof for what purposes the ultrasound system has been used. However, this system also may be subject to tampering and appears to be disadvantageous in this respect.

CN 1915177 A discloses a method for discriminating and recording the sex of fetus by ultrasonography B including steps as using the probe of ultrasonography B to obtain and display the image of fetus, recognizing the image for judging if it has sexual organ, and recording the sex of fetus if the display frequency of the fetus image containing sexual organ is higher than a predefined normal frequency.

In addition to ultrasound, the government of India and various other governments are starting to bring other imaging modalities under these laws, such as MRI and CT. No known solution exists for these modalities.

SUMMARY OF THE INVENTION

It is an object of the present invention to provide a device, method and computer program for monitoring a medical imaging system in order to more efficiently prevent the misuse of the system for gender detection compared to systems of the prior art.

In a first aspect of the present invention a device for detecting a misuse of a medical imaging system is presented, comprising:
  a data interface for acquiring medical image data and audit log data from the medical imaging system;
  a processing unit which is configured to analyse the medical image data to determine whether or not a part of a fetus is imaged in the medical image data, to compare the medical image data and the audit log data with each other if it is determined that a part of a fetus is imaged in the medical image data, and to determine based on said comparison whether there is a mismatch between the medical image data and the audit log data; and
  a feedback unit which is configured to generate a misuse alert signal if a mismatch is detected by the processing unit.

In a further aspect of the present invention a corresponding method is presented which comprises the steps of
  acquiring medical image data and audit log data from the medical imaging system;
  analysing the medical image data to determine whether or not a part of a fetus is imaged in the medical image data;

comparing the medical image data and the audit log data with each other if it is determined that a part of a fetus is imaged in the medical image data;

determining based on said comparison whether there is a mismatch between the medical image data and the audit log data; and generating a misuse alert signal if a mismatch is detected.

In a still further aspect of the present invention a computer program is presented which comprises program code means for causing a computer to carry out the steps of the above-mentioned method when said computer program is carried out on a computer.

Thus, the herein presented system and method correlate the information extracted from the medical image system log with the actual images seen on the machine. The audit log data and the medical imaging data are matched with each other to see whether there occurs any mismatch between the two data sets that might identify a misuse of the medical imaging system.

Audit log data in the meaning of the present invention relate to a data set of records that may be chronological and that provides documentary evidence of the sequence of activities performed on and with the medical imaging system. The audit log data may, for example, comprise information about the following: when was the medical imaging system used, for how long was the medical imaging system used, for what was the medical imaging system used, and/or by whom was the medical imaging system used.

A medical imaging system in the meaning of the present invention may include but is not limited to an ultrasound imaging system, a CT imaging system, or a MRI imaging system.

By checking the medical image data against the audit log data any irregularity pointing at a misuse or tampering of the medical imaging device may be discovered.

The processing unit may be configured to detect e.g. at least one of the following:

(i) if one of the medical images indicated in the audit log data as being recorded is missing in the medical image data;

(ii) if there is a mismatch between an image type indicated in the audit log data and an image type of the medical images contained in the medical image data;

(iii) if there is mismatch between a user identification indicated in the audit log data and a user identification indicated in the medical image data;

(iv) if there is a mismatch in an activity type indicated in the audit log data and an activity type indicated in the medical image data;

(v) if there is a mismatch between a focus with which an image indicated in the audit log data has been acquired and a focus with which the image indicated in the medical image data has been acquired;

(vi) if there is a mismatch between an operating frequency with which an image indicated in the audit log data has been acquired and an operating frequency with which the image indicated in the medical image data has been acquired;

(vii) if there is a mismatch between a recording time indicated in the audit log data and a recording time indicated in the medical image data; and (viii) if there is a mismatch between a file size of an image indicated in the audit log data and a file size of the image indicated in the medical image data.

The processing unit is thus configured to detect a predetermined misuse pattern, e.g. one of the above-mentioned types, to determine based on the comparison/matching between the medical image data and the audit log data whether there is any mismatch between the two data sets. If any such pattern indicating tampering of the medical imaging device is detected, it can be used as a trigger point for further action. In this case a misuse alert signal is generated by a feedback unit. This misuse alert signal may trigger several possible actions, as they will be described further below in detail. Possible actions are a generation of a notification that is send to a relevant authority, or the generation of a report that is stored in a secured database.

The present invention therefore helps preventing a misuse of a medical imaging device, especially a misuse of the device for gender detection in countries where such a prenatal gender detection is prohibited by law.

In a further refinement, the acquired medical image data are encrypted to even more effectively prevent any kind of digital tampering.

According to the present invention, the processing unit is configured to analyse the medical image data to determine whether or not a part of a fetus is imaged in the medical image data.

This allows automatically identifying whether the medical image data result from an obstetric medical scan (including an imaged part of a fetus) or from a non-obstetric medical scan (not including any imaged part of a fetus). Identifying a type of anatomy being scanned allows an automatic logging of the medical activities (type of scan), thus potentially reducing the effort required to meet the regulatory requirements for preventing misuse for fetal sex determination, and thereby supporting the penetration of medical imaging systems for non-obstetric applications in countries like India.

The processing unit is further configured to compare the medical image data and the audit log data with each other only if it is determined that a part of a fetus is imaged in the medical image data.

This allows decreasing the processing and computing effort, since the above-mentioned matching between the medical image data and the audit log data is performed only in case of an obstetric scan, whereas the matching is not performed if the medical image data are identified to contain only non-obstetric data that are not in focus of the above-mentioned law acts for prohibiting fetal sex determination.

According to an embodiment, the processing unit is configured to determine whether or not a part of a fetus is imaged in the medical image data based on a feature-based algorithm.

This feature-based algorithm may comprise an image processing technique, such as an edge detection and/or segmentation, in order to identify typical medical and anatomical features of a fetus, such as e.g. parts of a face or other body parts in an expected size range.

This feature-based algorithm is preferably implemented in conjunction with a deep learning neural network. Deep learning neural networks is an application to learning tasks of artificial neural networks that contain more than one hidden layer. Deep learning is part of a broader family of machine learning methods based on learning data representations, as opposed to task specific algorithms. Such deep learning neural networks typically use a cascade of many layers of non-linear processing units for feature extraction and transformation. They are based on unsupervised learning of multiple levels of features or representations of the data, and learn multiple levels of representations that correspond to different levels of abstraction.

According to an embodiment of the present invention, the deep learning neural network is a convolutional neural network. A convolutional neural network is a class of deep, feed-forward artificial neural network that has been successfully applied to analysing visual imagery. Convolutional neural networks were inspired by biological processes in which the connectivity pattern between neurons is inspired by the organization of the animal visual cortex. Convolutional neural networks use a variation of multi layer perceptrons designed to require minimal preprocessing.

In case of the usage of such a convolutional neural network within the processing unit of the presented device, a plurality of layers and sub-layers of convnet are provided.

According to a further embodiment of the present invention, the data interface of the presented device is configured to acquire the medical image data via a first data channel and to acquire the audit log data via a second data channel that is different from the first data channel.

For example, the medical image data could be transferred to the processing unit using a video or image grabber card, and the audit log data could be transferred to the processing unit using a separate wired or wireless connection. Acquiring the two data sets via separate data channels increases the protection against manipulation of the medical imaging system.

According to a further embodiment of the present invention, the data interface is configured to further acquire an uptime of the medical imaging system, wherein the processing unit is configured to compare the medical image data and/or the audit log data to the uptime of the medical imaging system.

The device may thus also check the system uptime information so as to check the validity of the usage time. This information may be matched against approved criteria. If a pattern of violation is detected, a misuse alert signal is generated.

As already mentioned above, generating the misuse alert signal may comprise several actions. In one alternative, generating the misuse alert signal comprises sending an electronic message to a server that is connected to the device via a data network, e.g. via the Internet. Additionally or in another alternative, generating the misuse alert signal may comprise generating a report and saving the report in a memory or cloud. It may also comprise sending medical image data that are found to be suspicious to another server of cloud. Still further, generating the misuse alert signal may comprise displaying a message as warning to the user via a display and/or saving an electronic message, a report, and/or medical image data on a local hard drive. Relevant authorities may thus easily check whether the medical imaging device was manipulated and/or misused for prenatal sex determination.

These and other embodiments of the invention are defined in the dependent claims. It shall be understood that the claimed method and the claimed computer program have similar and/or identical preferred embodiments as the claimed device and as defined in the dependent claims.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
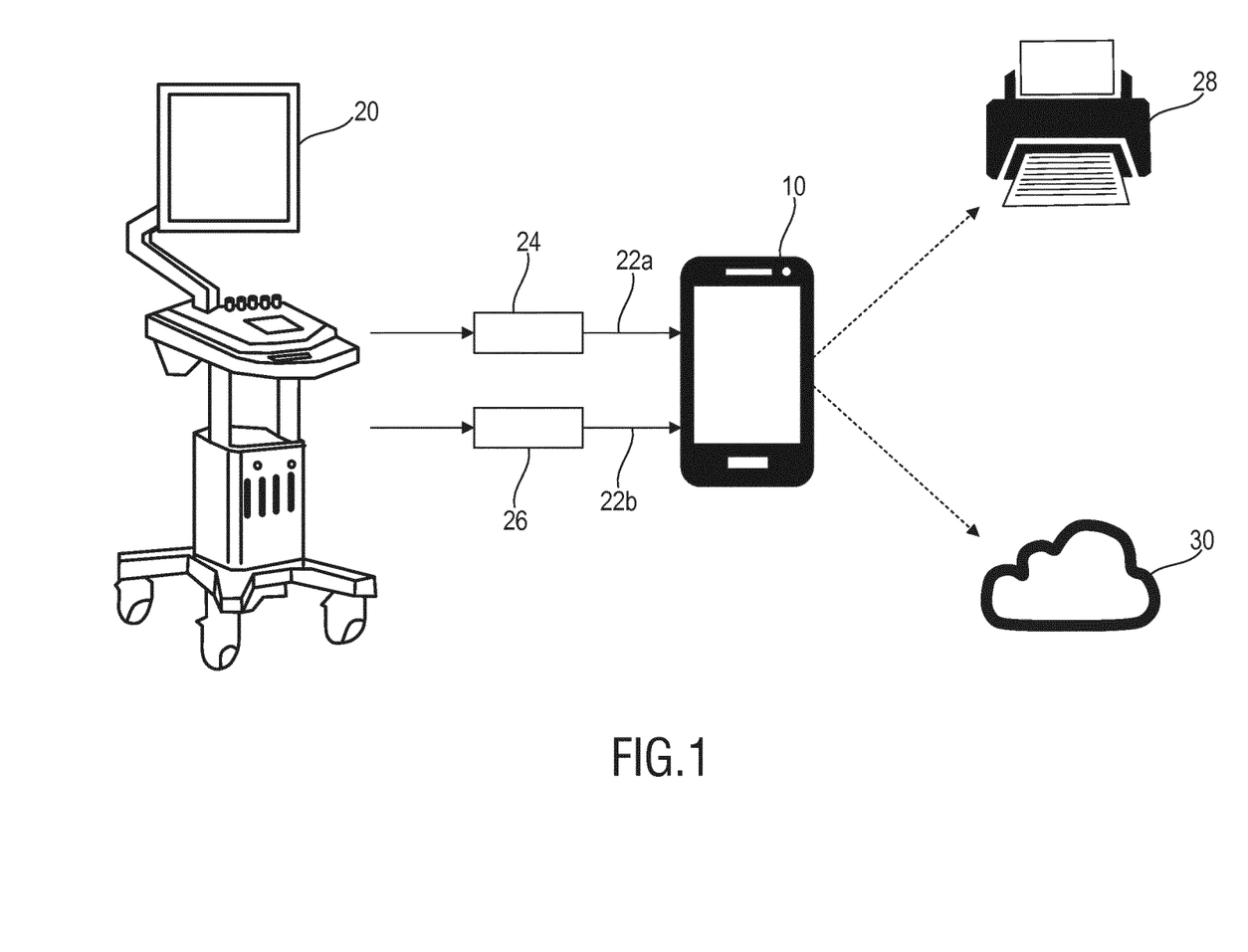
FIG. 1 shows a schematic representation of an implementation of the herein presented device according to an embodiment.

FIG. 1 schematically illustrates how the device according to the present invention may be used in practice according to an embodiment.

Figure 2:
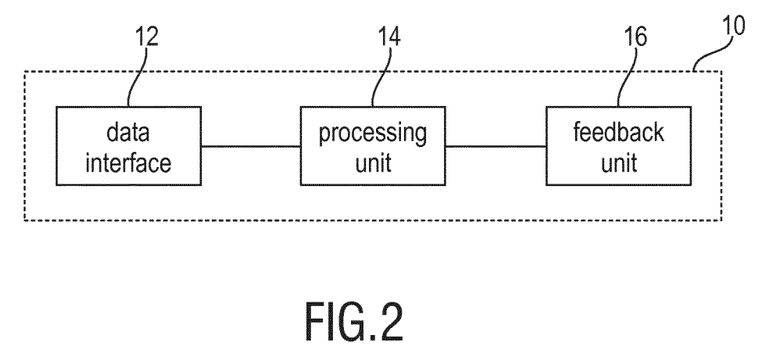
FIG. 2 shows a block diagram illustrating the components of the herein presented device according to an embodiment.

FIG. 2 schematically illustrates possible components of the herein presented device in a block diagram. The device according to the present invention is therein indicated with reference numeral 10.

In the example shown in FIG. 1, the device 10 is implemented as a mobile computing device, e.g. a smartphone or a tablet PC. However, this is only one exemplary implementation. The device 10 may also be implemented in a PC, a server, or in any other computing device.

The device 10 is connected to an ultrasound imaging system 20 via one or more hard-wired or wireless data connection 22a, 22b. The device 10 comprises a data interface 12, a processing unit 14, and a feedback unit 16 (see FIG. 2). These components 12, 14, 16 of the device 10 are preferably, but not necessarily implemented as separate hardware units within the device 10. However, it shall be noted that some of the units 12, 14, 16 may also be implemented in one and the same hardware unit. The device 10 may comprise further units/components in addition to those schematically illustrated in FIG. 2.

The data interface 12 is configured to acquire data from the ultrasound imaging system 20. In a preferred embodiment, the data interface 12 receives from the ultrasound imaging system 20 ultrasound image data 24 and audit log data 26. These two data types 24, 26 are preferably received via different data channels 22a, 22b. The ultrasound image data 24 may exemplarily be transferred to the device 10 via a video grabber card. The audit log data 26 may exemplarily be transferred by means of a Bluetooth®, a USB interface, or any other wireless or hard-wired data interface. The data 24, 26 are either sent to the device 10 on a continuous basis or on a periodic basis.

The processing unit 14 is preferably implemented as a CPU. The processing unit 14 is configured to perform a matching between the ultrasound image data 24 and the audit log data 26 so as to determine based on said matching if there is a mismatch between the ultrasound image data 24 and the audit log data 26. The ultrasound image data are in other words checked against the audit log data in order to identify any irregularities that might arise from a manipulation or tampering of the ultrasound imaging system 20. This may be particularly used to support official authorities in detecting unauthorized fetal sex determination in countries where this is prohibited by law.

The feedback unit 16 is configured to generate a misuse alert signal if a mismatch is detected by the processing unit 14. The misuse alert signal may trigger several possible actions. The feedback unit 16 may be configured to generate a report regarding the matching of the ultrasound image data 24 with the audit log data 26. This report may be used to alert official authorities. The report may e.g. be sent to a printer 28 residing at an official authority. Alternatively, the report or alert may be sent via the Internet to a cloud server 30. According to a further alternative, the report or alert may be sent to a remote data server or saved on a local hard drive within the device 10.

The report or alert may include a filled out regulatory form indicating whether approved criteria of the usage of the ultrasound imaging system 20 are met or not. The report or alert may furthermore include a visualization of approved and unapproved usage of the ultrasound imaging system 20, a tracking of alerts, longterm analysis of a usage pattern of the ultrasound imaging system 20, etc.

In summary, this means that the device 10 correlates the ultrasound image data 24 extracted from the ultrasound imaging system 20 with the audit log data 26 of the ultrasound imaging system 20. Any mismatch between the two data sets 24, 26 is identified and a usage pattern is created. If a pattern indicating tampering or misuse of the ultrasound imaging system 20 is detected, this is used as a trigger point for further action, wherein the goal of said action is primarily a prevention of misuse of the ultrasound imaging system 20 for prenatal gender detection.

The processing unit 14 may e.g. be configured to check whether the ultrasound image data 24 include all images indicated in the audit log data 26 as recorded. If one image is missing in the ultrasound imaging data 24, this could be an indicator that the image has been manually deleted. The processing unit 14 may also be configured to check whether the data type indicated in the audit log data 26 corresponds to the data type of the ultrasound images contained in the ultrasound image data 24. Similar checks may be made regarding the data of the users of the ultrasound imaging system 20, the usage time, the data size, and the type of ultrasound acquisition.

Figure 3:
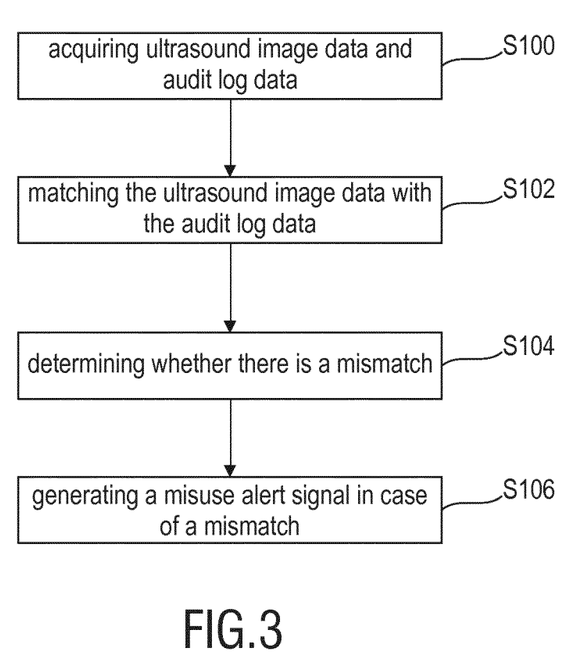
FIG. 3 shows a schematic block diagram illustrating a first embodiment of the herein presented method.

FIG. 3 summarizes the herein presented method according to a first embodiment. In a first step S100 the ultrasound image data 24 and the audit log data 26 are acquired from the ultrasound imaging system 20. In the next step S102, the ultrasound image data 24 and the audit log data 26 are compared/matched/correlated with each other. Then, in step S104, it is determined based in said comparison/matching/correlation whether there is a mismatch between the ultrasound image data 24 and the audit log data 26. Finally, in step S106, a misuse alert signal may be generated if a mismatch is detected in step S104.

Figure 4:
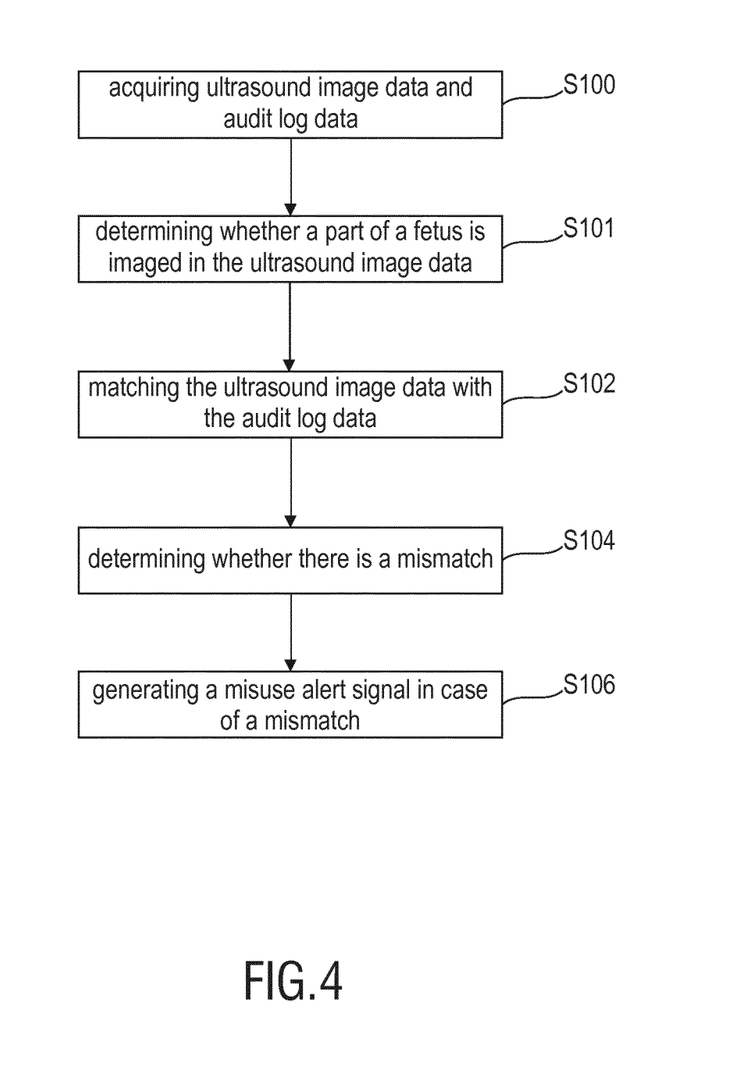
FIG. 4 shows a schematic block diagram illustrating a second embodiment of the herein presented method.

FIG. 4 shows a second embodiment of the herein presented method. The method according to this embodiment comprises an additional method step S101. In this method step S101 it is determined whether a part or a fetus is imaged in the ultrasound image data 24. It is in other words determined whether the ultrasound image data 24 result from an obstetric ultrasound scan or from a non-obstetric ultrasound scan. Step S101 may be used as an additional step in addition to step S102 or, in the alternative, it may be used as a prerequisite before performing S102. This means that the herein presented method and device 10 are implemented in such a way that the processing unit 14 is configured to perform the matching between the ultrasound image data 24 and the audit log data 26 only if it is determined that the ultrasound image data result from an obstetric ultrasound scan.

In step S101, it is preferably identified by means of image processing techniques what kind of anatomy is being imaged in the ultrasound image data. This identification is preferably based on an identification of the presence or absence of high level clinical features representing the fetal anatomy in the ultrasound image data 24. A deep learning algorithm is preferably used as a detector for the high-level clinical features. This deep learning algorithm is preferably implemented as a convolutional neural network comprising a plurality of layers and sub-layers and abstracting higher level clinical features of the fetal anatomy in ultrasound images from the first trimester to the third trimester.

FIGS. 5-8 show four different embodiments how this deep learning based detector used in step S101 may be implemented in practice.

Figure 5:
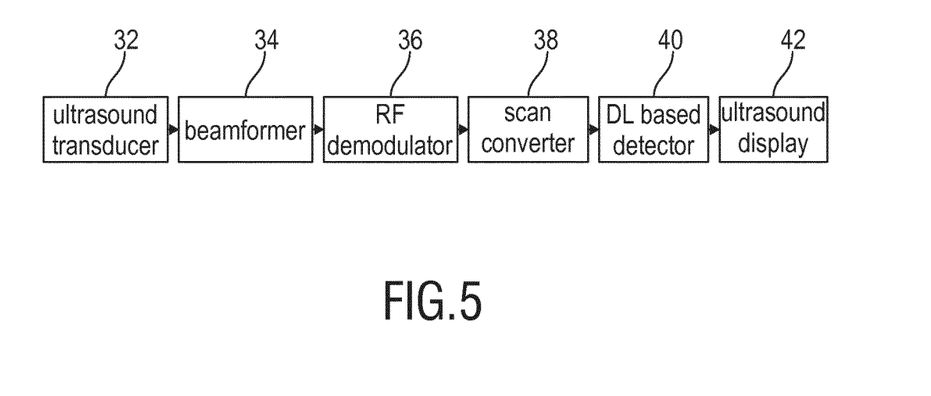
FIG. 5 shows a schematic block diagram illustrating a part of the herein presented method according to a first example.

In the first embodiment illustrated in FIG. 5 the deep learning neural network is implemented in the ultrasound imaging system 20 itself. The ultrasound image data are thus generated in a conventional way: first acquired by an ultrasound transducer 32, then beamformed by a beamformer 34, transferred to a RF demodulator 36, further to a scan converter 38. The thereby generated ultrasound images are then fed in the deep learning neural network, where it is detected whether the ultrasound images result from an obstetric scan or a non-obstetric scan. The result of this detection may finally be shown on a display 42 of the ultrasound imaging system 20. The result is preferably also stored in the audit log data 26.

Figure 6:
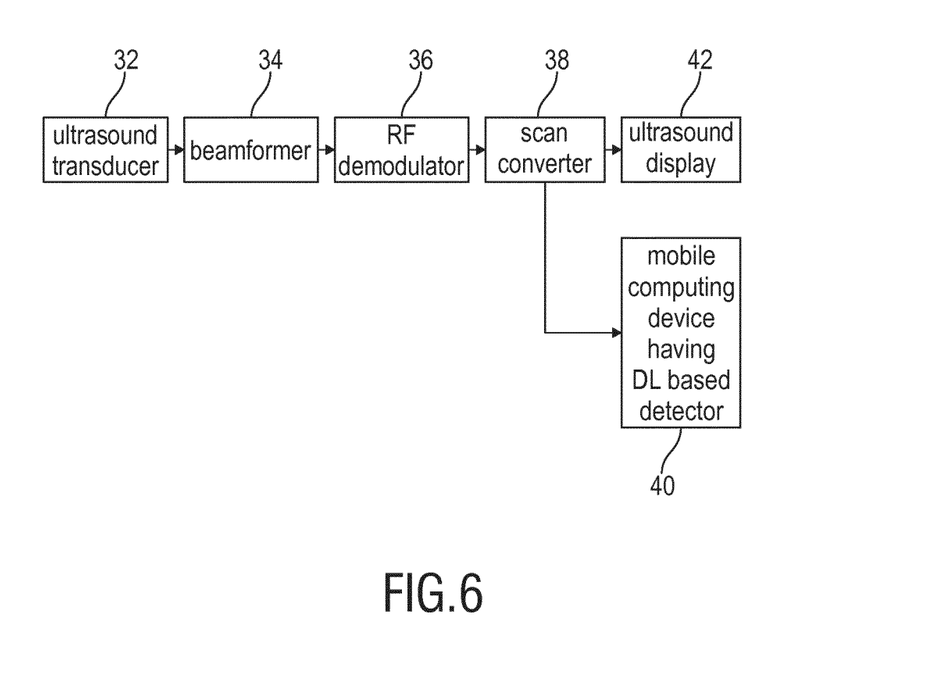
FIG. 6 shows a schematic block diagram illustrating a part of the herein presented method according to a second example.

In the second example that is schematically illustrated in FIG. 6 the ultrasound image data 24 generated by the ultrasound imaging system 20 are transferred to a mobile computing device having the deep learning based detector 40 stored thereon. A DNL protocol may be used to continuously stream the 2D/3D ultrasound image data from the ultrasound system 20 to the mobile computing device. DNL is a feature provided in ultrasound systems via which 2D/3D ultrasound image data may be streamed to a TCP/IP connected mobile computing device, such as a laptop, PC or workstation. The 2D/3D image data may be displayed on the mobile computing device. Within the mobile computing device the 2D/3D ultrasound images are passed to the deep learning based detector which finally outputs the detection result whether the ultrasound image data 24 result from an obstetric or non-obstetric scan.

Figure 7:
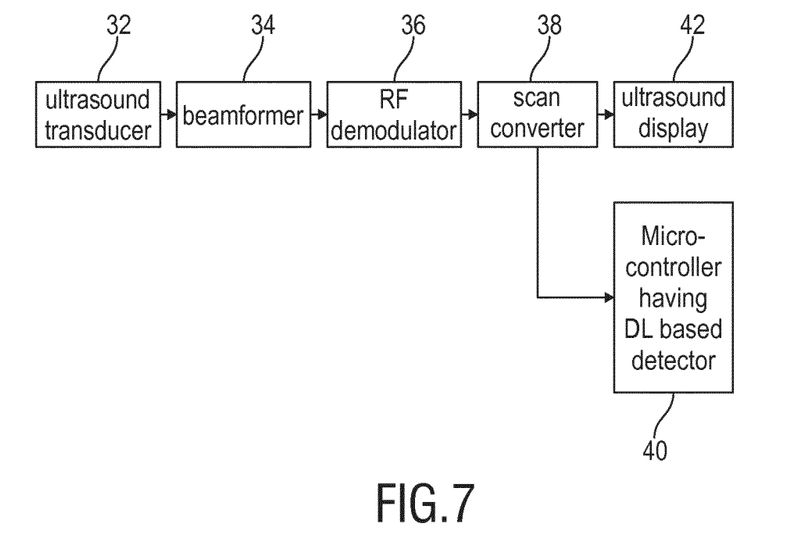
FIG. 7 shows a schematic block diagram illustrating a part of the herein presented method according to a third example.

Alternatively, the ultrasound image data 24 may be transferred to a micro controller via an S-video or composite video data interface (see FIG. 7). Of course, the S-video data interface may also be used to transfer the ultrasound image data 24 to a laptop, a PC or a workstation system. In the embodiment shown in FIG. 7 the method step S101 is implemented as an additional hardware peripheral device which receives the continuously streamed 2D/3D image data from the ultrasound imaging system 20 via the S-video output interface. Similar as in the previous embodiments, the 2D/3D ultrasound images are passed on to the deep learning neural network in order to identify whether the 2D/3D images result from an obstetric of non-obstetric scan.

Figure 8:
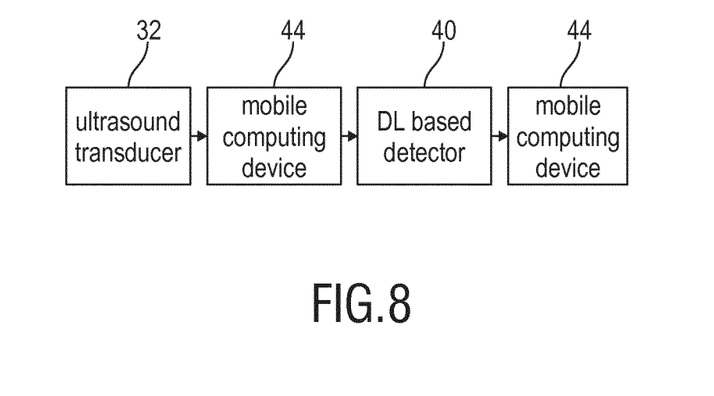
FIG. 8 shows a schematic block diagram illustrating a part of the herein presented method according to a fourth example.

FIG. 8 illustrates an embodiment which could be used for ultra mobile ultrasound systems, where the ultrasound transducer 32 is connected to a mobile computing device 44, such as a mobile phone or a tablet PC, e.g. via USB. The ultrasound transducer 32 is in this embodiment thus directly connected to the mobile computing device 44. For example for Android-based tablets and smartphones, a couple of background processes may be used to implement the deep learning neural network based detector. The implementation Android Media Projection may be used to access the latest frame buffer (H/W composed) in the buffer queue. Once the ultrasound probe is connected, the app (deep learning based scan detector) gets started. During every callback from the Media Projection class with frame data, the required B-mode ROI is cropped, downsample the frame, convert to NV21 (YUV420sp) format and pass the pixel data to the deep learning neural network. The output of the deep learning based detector may then be sent to another mobile computing device, a cloud server of any other remote server system.

Independent which of the afore-mentioned embodiments are used, the deep learning neural network is preferably realized as a convolutional neural network model having multiple layers of convnet and also sub-layers of convnet interconnected. A convnet contains three main layers (convolution layer, normalization layer and pulling layer) followed by a fully connected layer. There may be three convnet layers followed by three fully connected layers.

While the implementation with a convolutional neural network is one way for implementing method step S101, it shall be noted that also other techniques may be used for implementing said method step.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

Although the aforementioned embodiments are described with reference to ultrasound imaging systems, the present invention is not limited to the field of ultrasound imaging. In other embodiments, the image and log analysis could be done with images and log data coming from modalities other than ultrasound, such as MRI, CT or any other diagnostic systems that can be used for sex determination.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for detecting a misuse of a medical imaging system, comprising:
    a data interface for acquiring medical image data and audit log data from the medical imaging system;
    a processing unit which is configured to analyse the medical image data to determine whether or not a part of a fetus is imaged in the medical image data, to compare the medical image data and the audit log data with each other if it is determined that a part of a fetus is imaged in the medical image data, and to determine based on said comparison whether there is a mismatch between the medical image data and the audit log data; and
    a feedback unit which is configured to generate a misuse alert signal if a mismatch is detected by the processing unit.

2. The device according to claim 1, wherein the audit log data is a data set of records that provides documentary evidence of a sequence of activities performed on and with the medical imaging system, the audit log data comprising information about at least one of the following: when was the medical imaging system used, for how long was the medical imaging system used, for what was the medical imaging system used, and by whom was the medical imaging system used.

3. The device according to claim 1, wherein the processing unit is configured to determine based on said comparison at least one of the following:
    (i) if one of medical images indicated in the audit log data as being recorded is missing in the medical image data;
    (ii) if there is a mismatch between an image type indicated in the audit log data and an image type of the medical images contained in the medical image data;
    (iii) if there is mismatch between a user identification indicated in the audit log data and a user identification indicated in the medical image data;
    (iv) if there is a mismatch in an activity type indicated in the audit log data and an activity type indicated in the medical image data;
    (v) if there is a mismatch between a focus with which an image indicated in the audit log data has been acquired and a focus with which the image indicated in the medical image data has been acquired;
    (vi) if there is a mismatch between an operating frequency with which an image indicated in the audit log data has been acquired and an operating frequency with which the image indicated in the medical image data has been acquired;
    (vii) if there is a mismatch between a recording time indicated in the audit log data and a recording time indicated in the medical image data; and
    (viii) if there is a mismatch between a file size of an image indicated in the audit log data and a file size of the image indicated in the medical image data.

4. The device according to claim 1, wherein the processing unit is configured to determine whether or not a part of a fetus is imaged in the medical image data based on a feature-based algorithm.

5. The device according to claim 1, wherein the processing unit is configured to determine whether or not a part of a fetus is imaged in the medical image data using a deep learning neural network.

6. The device according to claim 5, wherein the deep learning neural network is a convolutional neural network.

7. The device according to claim 6, wherein the convolutional neural network comprises a plurality of layers and sub-layers.

8. The device according to claim 1, wherein the data interface is configured to acquire the medical image data via a first data channel and to acquire the audit log data via a second data channel that is different from the first data channel.

9. The device according to claim 1, wherein the data interface is configured to further acquire an uptime of the medical imaging system, and wherein the processing unit is configured to compare the medical image data and/or the audit log data to the uptime of the medical imaging system.

10. The device according to claim 1, wherein the processing unit is configured to detect a predetermined misuse pattern to determine based on said comparison whether there is a mismatch between the medical image data and the audit log data.

11. The device according to claim 1, wherein generating the misuse alert signal comprises sending an electronic message to a server that is connected to the device via a data network.

12. The device according to claim 1, wherein generating the misuse alert signal comprises generating a report and saving the report in a memory or cloud.

13. The device according to claim 1, wherein the device is a mobile computing device which is connected to the medical imaging system via a hard-wired or wireless connection.

14. A method for detecting a misuse of a medical imaging system, comprising the steps of:
- acquiring medical image data and audit log data from the medical imaging system;
- analysing the medical image data to determine whether or not a part of a fetus is imaged in the medical image data;
- comparing the medical image data and the audit log data with each other if it is determined that a part of a fetus is imaged in the medical image data;
- determining based on said comparison whether there is a mismatch between the medical image data and the audit log data; and
- generating a misuse alert signal if a mismatch is detected.

15. A non-transitory computer program stored on a computer-readable medium, comprising program code that in response to execution on a processor cause the actions of the method recited in claim 14.

* * * * *